(12) United States Patent
Apkarian et al.

(10) Patent No.: US 11,452,604 B2
(45) Date of Patent: Sep. 27, 2022

(54) SYSTEMS AND METHODS FOR TREATING REGURGITATING CARDIAC VALVES

(71) Applicant: Boston Scientific Scimed, Inc., Maple Grove, MN (US)

(72) Inventors: Kalyna L. Apkarian, Minneapolis, MN (US); Thomas P. Jancaric, Maple Grove, MN (US); Reggie Roth, Monticello, MN (US); Umang Anand, Plymouth, MN (US); Dennis B. Werner, Big Lake, MN (US); Jason A. Kilvington, Shoreview, MN (US); James K. Cawthra, Jr., Ramsey, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 122 days.

(21) Appl. No.: 16/695,523

(22) Filed: Nov. 26, 2019

(65) Prior Publication Data

US 2020/0163768 A1 May 28, 2020

Related U.S. Application Data

(60) Provisional application No. 62/771,876, filed on Nov. 27, 2018.

(51) Int. Cl.
*A61F 2/24* (2006.01)

(52) U.S. Cl.
CPC ............ *A61F 2/2466* (2013.01); *A61F 2/243* (2013.01); *A61F 2/246* (2013.01); *A61F 2/2412* (2013.01); *A61F 2/2454* (2013.01)

(58) Field of Classification Search
CPC ...... A61F 2/2466; A61F 2/246; A61F 2/2412; A61F 2/243; A61F 2/2454
See application file for complete search history.

(56) References Cited

U.S. PATENT DOCUMENTS

| 4,978,304 A | * | 12/1990 | Alexander | ............... G09B 9/00 36/136 |
| 6,764,510 B2 | | 7/2004 | Vidlund et al. | |
| 8,500,733 B2 | * | 8/2013 | Watson | ............. A61M 25/0141 606/41 |
| 9,636,223 B2 | | 5/2017 | Khalil et al. | |
| 2003/0120341 A1 | | 6/2003 | Shennib et al. | |

(Continued)

FOREIGN PATENT DOCUMENTS

| EP | 2114304 A1 | * | 11/2009 | ........... A61F 2/0077 |
| EP | 2114304 B1 | * | 9/2017 | ............... A61F 2/24 |

(Continued)

OTHER PUBLICATIONS

International Search Report and Written Opinion for the International Patent Application No. PCT/US2019/063164, dated Feb. 18, 2020, 10 pages.

*Primary Examiner* — Jerrah Edwards
*Assistant Examiner* — Jared Klar Rovira
(74) *Attorney, Agent, or Firm* — Seager, Tufte & Wickhem LLP

(57) ABSTRACT

The present disclosure relates generally to the field of medical devices. In particular, the present disclosure relates to medical devices, systems and methods to treat a regurgitating cardiac valve, including, for example a tricuspid or mitral valve.

20 Claims, 8 Drawing Sheets

(56) References Cited

U.S. PATENT DOCUMENTS

| | | | |
|---|---|---|---|
| 2007/0255399 A1* | 11/2007 | Eliasen | A61F 2/246 623/2.36 |
| 2007/0282429 A1 | 12/2007 | Hauser et al. | |
| 2011/0264208 A1 | 10/2011 | Duffy et al. | |
| 2013/0325110 A1 | 12/2013 | Khalil et al. | |
| 2013/0338763 A1* | 12/2013 | Rowe | A61F 2/2427 623/2.11 |
| 2016/0242901 A1 | 8/2016 | Keren | |
| 2017/0143478 A1 | 5/2017 | Schwartz et al. | |
| 2017/0216028 A1 | 8/2017 | Khalil et al. | |
| 2018/0289480 A1* | 10/2018 | D'ambra | A61F 2/2451 |

FOREIGN PATENT DOCUMENTS

| | | | |
|---|---|---|---|
| WO | 2018218121 A1 | 11/2018 | |
| WO | WO-2018218121 A1 * | 11/2018 | A61F 2/24 |

\* cited by examiner

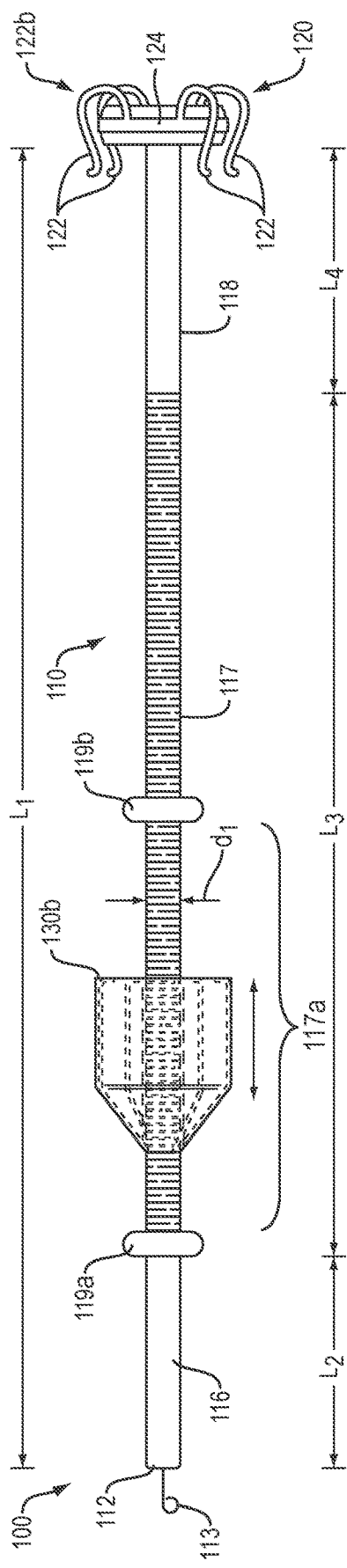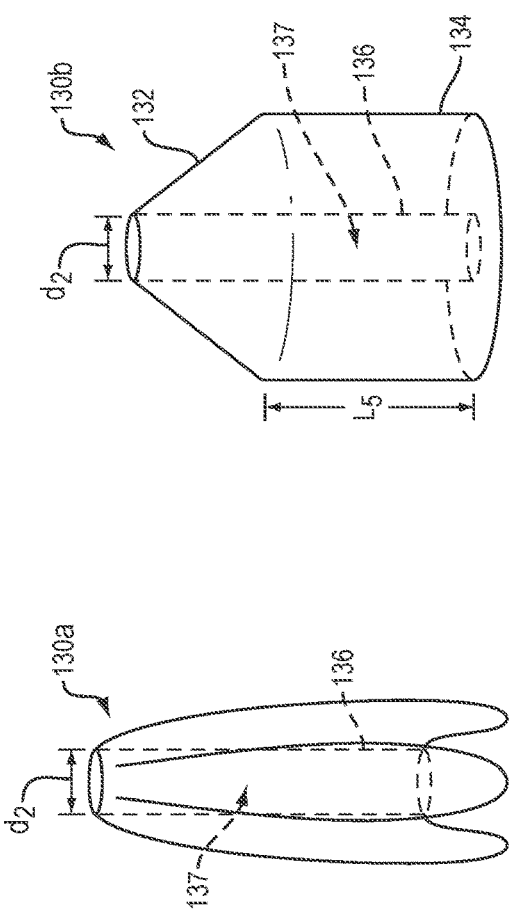
FIG. 1
FIG. 2A
FIG. 2B

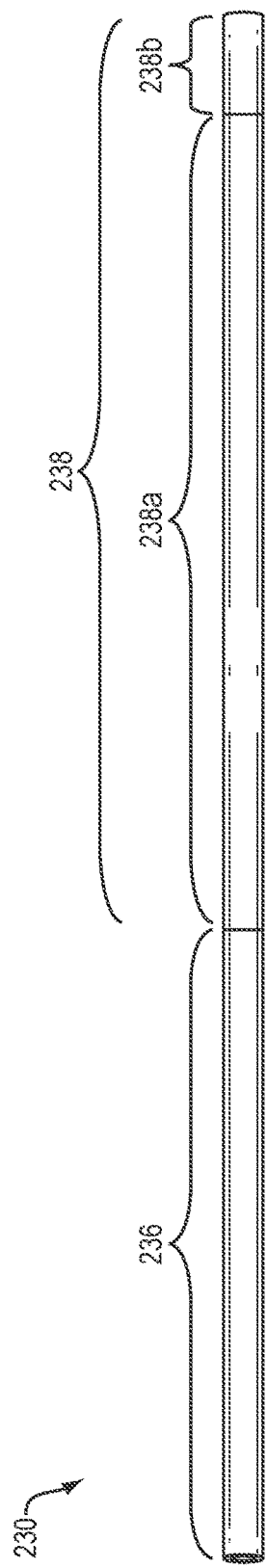
FIG. 3A
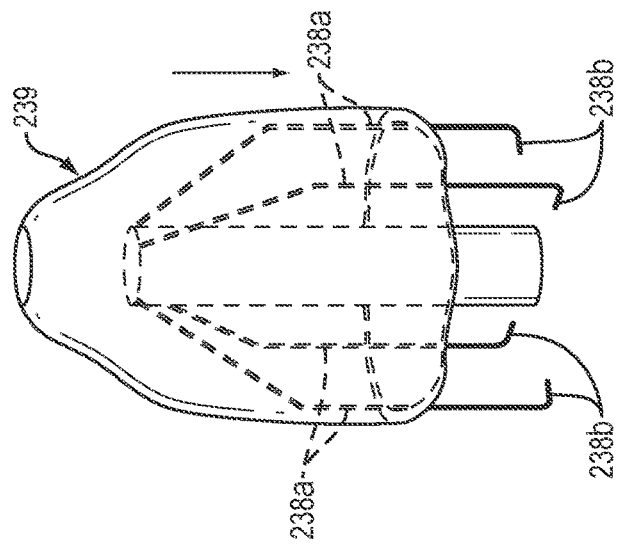
FIG. 3B
FIG. 3C

SYSTEMS AND METHODS FOR TREATING REGURGITATING CARDIAC VALVES

PRIORITY

This application claims the benefit of priority under 35 USC § 119 to U.S. Provisional Patent Application Ser. No. 62/771,876, filed Nov. 27, 2018, which is incorporated by reference herein in its entirety and for all purposes.

FIELD

The present disclosure relates generally to the field of medical devices. In particular, the present disclosure relates to medical devices, systems and methods to treat a defective cardiac valve, including, for example, a regurgitating tricuspid or mitral valve.

BACKGROUND

There are currently 1.6 million people in the United States living with moderate to severe cardiac valve regurgitation. If left untreated the mortality rate for individuals experiencing severe cardiac valve regurgitation is 64 percent. Open cardiac procedures to treat a regurgitating cardiac valve typically involve implanting an angioplasty ring around the defective valve. These open surgical procedures tend to have high rates of morbidity and mortality, especially considering the weakened or frail condition of most patients with a defective cardiac valve. Due to these high morbidity and mortality rates, less than 30 percent of individuals who require intervention undergo surgery.

A variety of advantageous medical outcomes may therefore be realized by the devices, systems and/or methods of the present disclosure, which provide a steerable transcatheter system for treating a regurgitating tricuspid or mitral cardiac valve in high risk patients.

SUMMARY

In one aspect, the present disclosure relates to a medical device comprising an elongate tether that may include a heat-set flexible middle portion and substantially rigid proximal and distal portions. An anchor may be disposed along a distal end of the tether. A plug may be slidably disposed along a proximal segment of the flexible middle portion. The flexible middle portion may be slotted. The substantially rigid proximal and distal portions may not be slotted. The anchor may be configured to engage a tissue wall of a right ventricle of a patient. The elongate tether may include a sufficient length to extend from the tissue wall of the right ventricle into the right atrium. The tether may be configured to substantially center the proximal segment of the flexible middle portion across the tricuspid valve of a patient. The plug may be configured to slide distally along the proximal segment of the middle portion when the right ventricle is in the diastole phase of the cardiac cycle, and the plug may be configured to slide proximally along the proximal segment of the middle portion when the right ventricle is in the systole phase of the cardiac cycle. The proximal segment of the flexible middle portion may be defined by first and second O-rings. The plug, when in a deployed configuration, may include a varying outer diameter proximal portion and a constant outer diameter distal portion. One or more leaflets of the tricuspid valve may contact an outer surface of the plug when the right ventricle is in the systole phase of the cardiac cycle. The plug may not contact any portion of the tricuspid valve when the right ventricle is in the diastole phase of the cardiac cycle. The anchor may include one or more retention members configured to move from a first configuration to a second configuration. The one or more retention members may extend beyond the distal end of the tether in the first configuration, and at least a portion of the one or more retentions members may extend over a segment of the rigid distal portion in the second configuration.

In another aspect, the present disclosure relates generally to a plug comprising a central spine, a framework extending over the central spin and an impermeable cover disposed around the framework. The plug may be configured to move from a first configuration to a second configuration. The framework, when in the second configuration, may include a varying outer diameter proximal portion and a constant outer diameter distal portion. The framework may comprise at least one strut extending over the central spine, and a tine may extend inward from a distal end of each of the at least one struts. A distal end of each tine may be configured to be attached to the central spine. The central spine and framework may be formed from a shape memory tube. The at least one strut and the tine may be formed as a plurality of cuts formed within in a first portion of the tube and folded back over a second portion of the tube. The constant outer diameter distal portion of the plug, when in the second configuration, may be configured to contact one or more leaflets of the tricuspid valve when in the systole phase of the cardiac cycle. The plug may be configured, when in the first configuration, to be slidably received within a lumen of a steerable delivery catheter.

In another aspect, the present disclosure relates generally to a system comprising a medical device slidably disposed within a lumen of a steerable delivery catheter. The medical device may include an elongate tether comprising a flexible middle portion and substantially rigid proximal and distal portions. An anchor may be disposed in a first configuration along a distal end of the tether. A plug may be disposed in a first configuration along a proximal segment of the flexible middle portion. A push rod may be slidably disposed within the lumen of the steerable delivery catheter and proximal to the medical device. The anchor and the plug may be configured to move from the first configuration to a second configuration when removed from constraint within the lumen of the steerable delivery catheter.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIG. 1 provides a perspective view of a medical device, according to one embodiment of the present disclosure.

FIGS. 2A-2B provide perspective views of a plug of a medical device in a collapsed (FIG. 2A) and expanded (FIG. 2B) configuration, according to one embodiment of the present disclosure.

FIGS. 3A-3C provide perspective views of a shape memory tube (FIG. 3A), which may be formed into a framework (FIG. 3B) and covered with a membrane or covering (FIG. 3C) to provide a plug of a medical device, according to one embodiment of the present disclosure.

DETAILED DESCRIPTION

Figure 4:
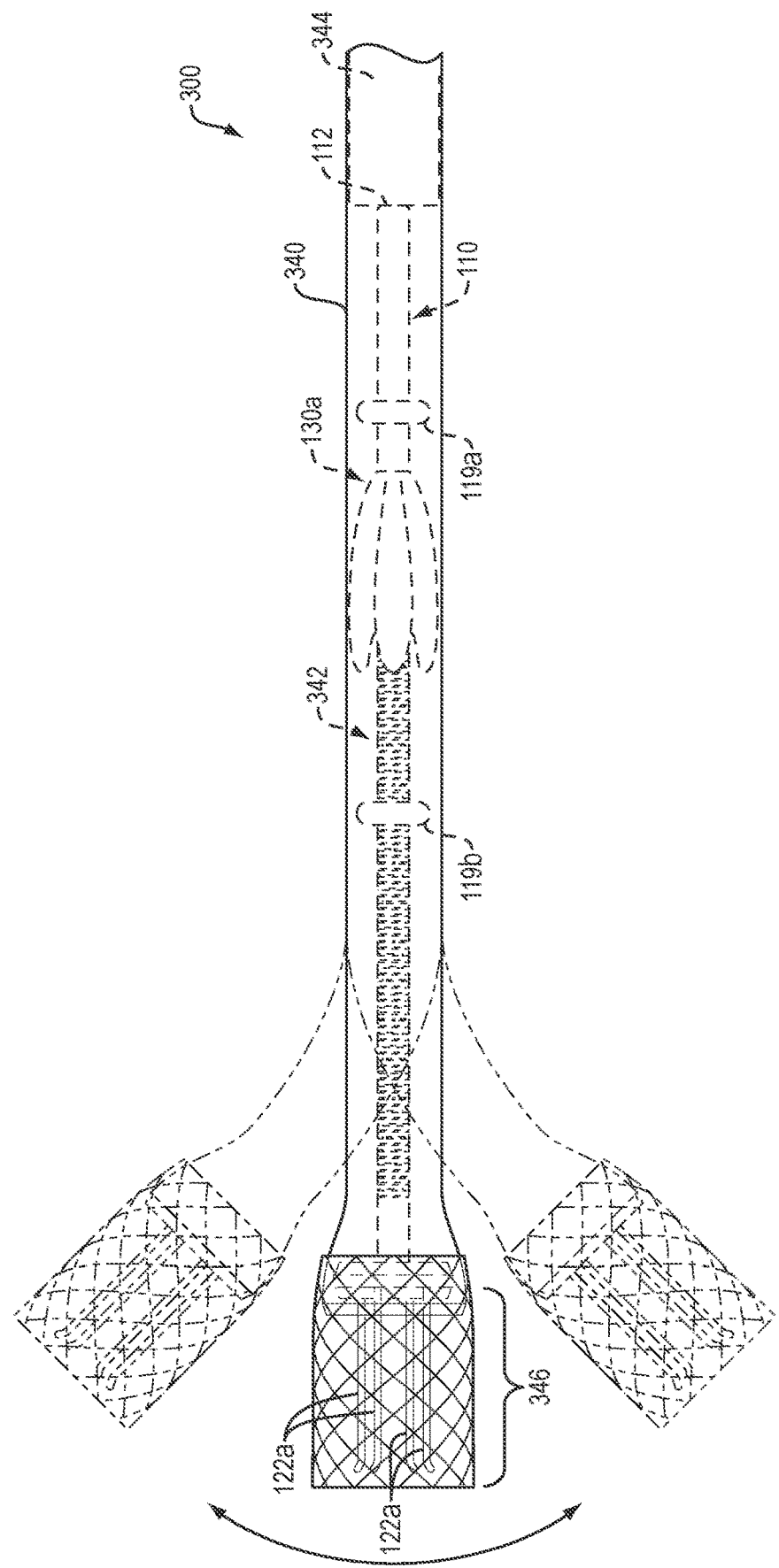
FIG. 4 provides a perspective view of a medical device disposed within a steerable delivery catheter, according to one embodiment of the present disclosure.

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure are described with specific reference to medical devices, systems and methods for treating a regurgitating tricuspid valve, it should be appreciated that such devices, systems and methods may be used to treat a variety of defective cardiac valves (e.g., atrioventricular valves), including, but not limited to the mitral valve.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

As used herein, the term "distal" refers to the end farthest away from the medical professional when introducing a device into a patient, while the term "proximal" refers to the end closest to the medical professional when introducing a device into a patient.

In various embodiments, the present disclosure relates to devices, systems and methods to treat a regurgitating, or otherwise defective, atrioventricular valve (e.g., a tricuspid valve or a mitral valve). Referring to FIG. 1, in one embodiment, a medical device 100 of the present disclosure may include an elongate tether 110 (e.g., rail, shaft, etc.) comprising a flexible middle portion 117 and substantially rigid proximal and distal portions 116, 118. In various embodiments, the tether 110 may be formed from or otherwise comprise a variety of biocompatible and durable shape memory materials, including, for example, nitinol. The proximal and distal portions 116, 118 may be substantially solid (e.g., non-slotted) to provide the desired rigidity and stability to maintain the medical device 100 properly positioned within the right ventricle of a patient (discussed below). The middle portion 117 may include a series of slots (e.g., laser cut slots) formed within a wall of the middle portion and along a length thereof to provide the desired characteristics of flexibility, rigidity and/or dampening. The elongate tether 110 may be heat-set, using techniques commonly known in the art, to provide the desired shape to the proximal 116, distal 118 and/or middle 117 portions when deployed within a cardiac chamber of a patient (discussed below).

In various embodiments, the non-slotted distal portion 118 may provide a substantially rigid "pivot point" for the flexible middle portion 117 to bend/move with the flow of blood during the cardiac cycle, and the non-slotted proximal portion 116 may provide a substantially rigid "platform" to interface with a delivery system (discussed below).

In various embodiments, the slots may be formed in a variety of patterns along all or a portion of the length and/or circumference of the middle portion 117. In addition, the width, length, depth, spacing (e.g., distance between adjacent slots), pattern (e.g., repeating or alternating), orientation (e.g., vertical or longitudinal) and/or shape (e.g., straight, curved, zig-zag, etc.) of the slots formed within the wall of the middle portion 117 may be varied to impart the desired flexibility/flexibilities to the middle portion. For example, the slots may include a width of approximately 0.001 inches to approximately 0.01 inches and a depth of approximately 0.0002 inches. In addition, or alternatively, the shape, width (e.g., outer diameter) and/or thickness (e.g., wall thickness) of the middle portion 117 may be varied to impart the desired flexibility/flexibilities to the middle portion. By way of non-limiting example, the proximal portion 116, middle portion 117 and/or distal portion 118, may include an outer diameter ($d_1$) of approximately 0.005 inches to approximately 0.021 inches.

In one embodiment, the slotted pattern and/or dimension of the middle portion 117 at or near the junction with the proximal portion 116 may be configured to minimize (e.g., dampen) the compressive load exerted on the distal portion 118 of the tether and/or anchor 120 as the plug 130 moves along the tether 110 (discussed below).

In one embodiment, the middle portion 117 of the tether 110 may include multiple heat-set angles, in which a first heat-set angle at or near the junction with the substantially straight distal portion 118 may provide the proper angle with the septal wall of the right atrium, a second heat-set angle may provide proper alignment with and/or centering across the tricuspid valve and a third heat-set angle at or near the junction with the substantially straight proximal portion 116 may provide the proper angle with the junction of the superior vena cava and the right atrium (e.g., the SVC/RA juncture). In addition to providing minimal interference with the flow of blood between cardiac chambers (e.g., the right atrium and right ventricle), the heat-set angle(s) of the middle portion 117 may allow the plug 130b to freely slide along the middle portion 117 (discussed below).

In various embodiments, the heat-set angle(s) may be approximately 45 degrees, but may also include a variety of angles ranging from approximately zero degrees to approximately 60 degrees.

In one embodiment, a distal end 114 of the tether 110 may include an anchor 120 (e.g., tissue anchor, etc.) configured to secure the medical device 100 within a cardiac wall of a patient's heart. The anchor 120 may include one or more retention members 122 (e.g., hooks, talons, barbs, clips, corkscrews, etc.) formed from or otherwise comprising a sufficiently bendable or deformable material (e.g., a shape memory material such as nitinol) such that each retention member 122 is individually configured to move from a first (e.g., constrained or delivery) configuration 122a (FIG. 4) to a second (e.g., unconstrained or deployed) configuration 122b (FIG. 1), in which a portion of each retention member 122 folds or bends back over/along a length of the distal portion 118. In one embodiment, a proximal end of each retention member 122 may be attached to, or integrally formed with, a platform or ring 124 extending around a portion of an outer surface of the anchor 120. In addition to providing an attachment point for the retention members 122, the larger outer diameter of the platform or ring 124 as compared to the outer diameter ($d_1$) of the tether may provide additional stability (e.g., increased surface area) for the tether 110 when attached to the cardiac wall. In various embodiments, the anchor 120 may be attached to the distal end 114 of the tether 110 using, for example, a suitable adhesive, glue, solder, resin, interference fit, or the like.

Although FIG. 1 depicts an embodiment which includes four retention members 122 arranged in a substantially symmetric or uniform configuration along/around a circumference of the anchor 120, in various embodiments, the size (e.g., approximately 2.0 mm to approximately 7.0 mm), shape, number, spacing and/or arrangement of the retention member(s) may vary, including, for example, a variety of different types of retention members disposed on or around the anchor 120.

A distal portion 346 of a (steerable) delivery catheter 340 (FIG. 4) may include an enlarged diameter portion to house the anchor 120 of the medical device 100 (discussed below). This range of outer diameters may allow a medical device 100 of the present disclosure to be slidably received within a standard (e.g., 23 French) delivery catheter 340 suitable for femoral or jugular access.

Figure 5A:
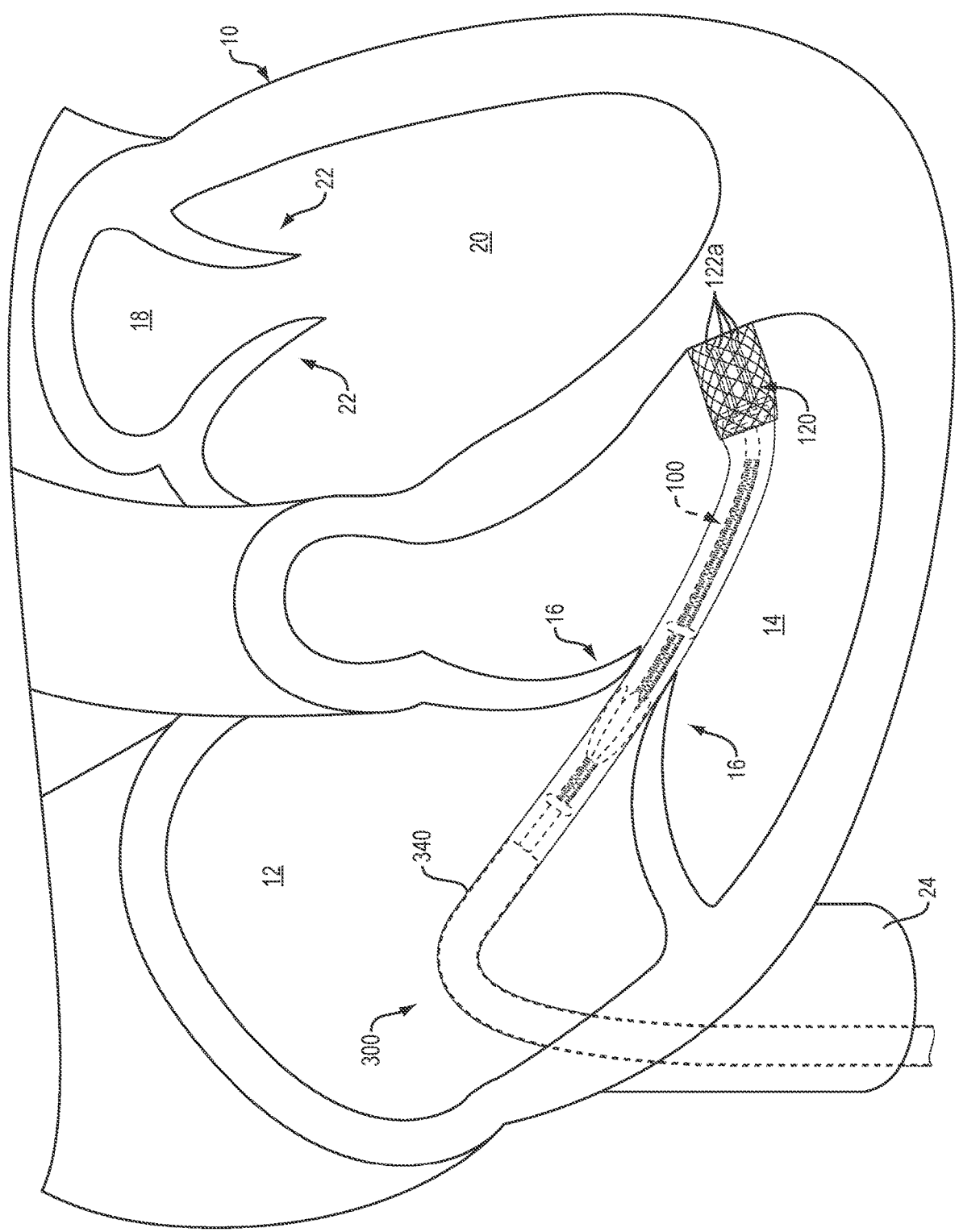
FIGS. 5A-5C provide schematic illustrations of a medical device being implanted within the heart of a patient, according to one embodiment of the present disclosure.
Figure 5B:
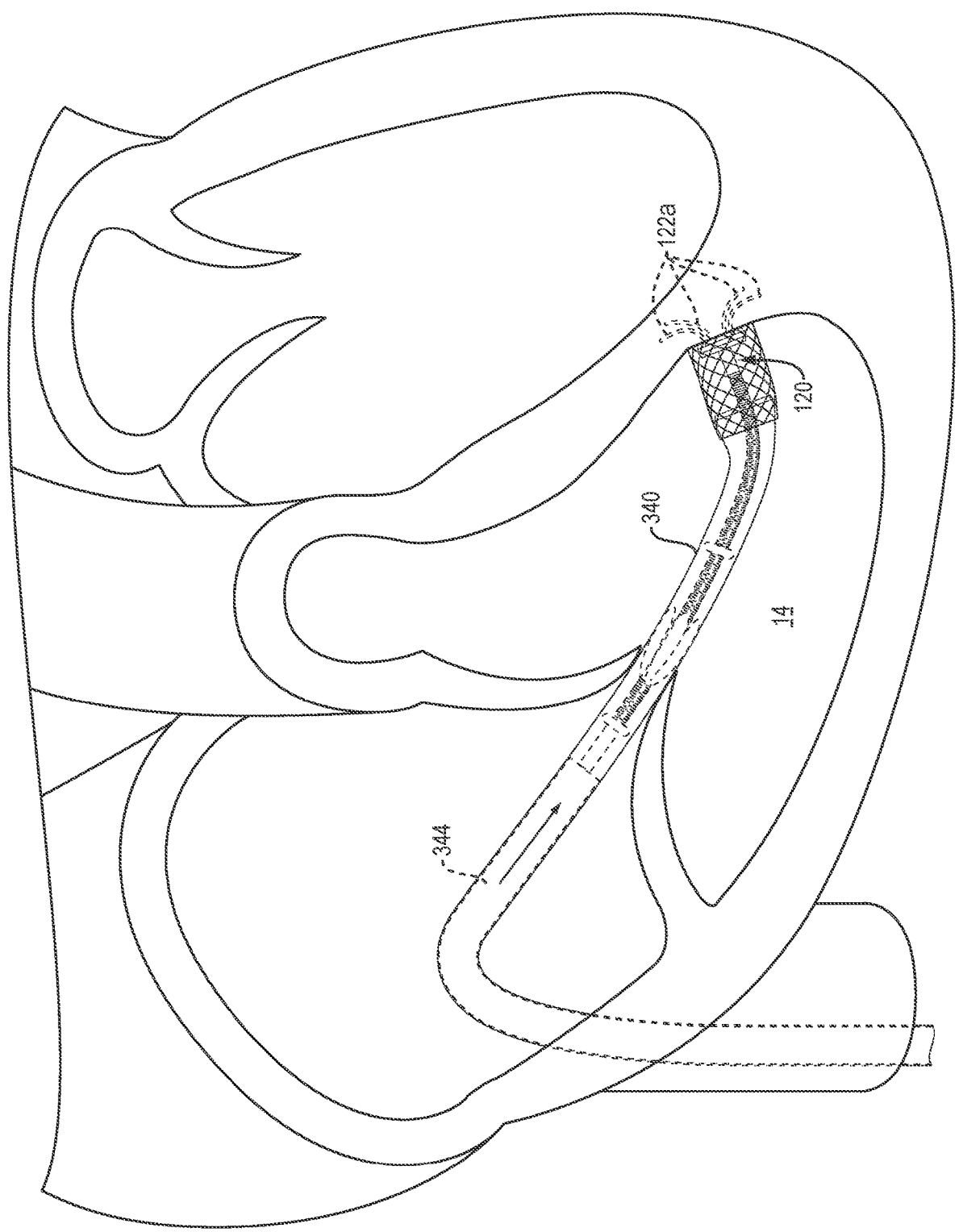
Figure 5C:
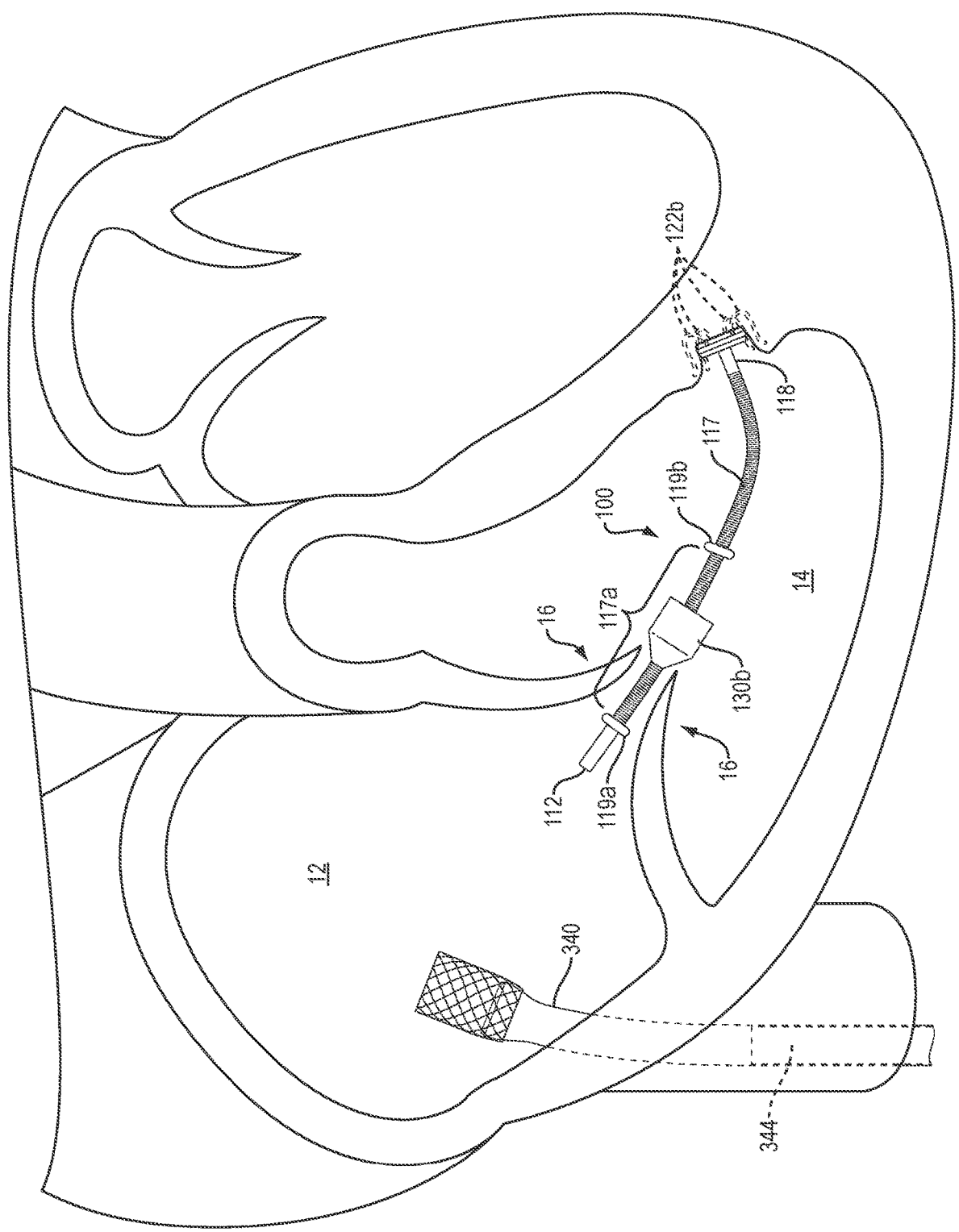

In one embodiment, a proximal end 112 of the tether 110 may include an engagement member 113 (e.g., hook, loop, clip, delivery platform, etc.) configured to reversibly receive a corresponding receiving element disposed on or along a distal end of a push rod 344 (FIG. 4) to assist in proper positioning of the medical device 100 upon deployment from a delivery system (FIGS. 5A-5C).

Still referring to FIG. 1, a plug 130b (e.g., buoy, heart valve coaptation member, valve leaflet coaptation member, etc.) may be slidably and rotatably disposed, e.g., in a deployed or expanded configuration, along a full or partial length of the middle portion 117 of the tether 110. In one embodiment, first and second O-rings 119a, 119b may be disposed around the middle portion 117 to define a segment 117a along which the plug 130b may slide. Although FIG. 1 depicts an embodiment in which the first O-ring 119a is disposed at an approximate junction between the proximal portion 116 and middle portion 117, and the second O-ring 119b is disposed at an approximate mid-point of the middle portion 117, in various embodiments the first and second O-rings 119a, 119b may be disposed along different segments of the middle portion, and/or separated by various distances, to adjust or tailor the length of the segment 117a along which the plug 130b may slide and/or rotate. For example, the first and second O-rings 119a, 119b may be separated by a distance of approximately 35.0 mm to approximately 40.0 mm along the middle portion 117. In one embodiment, the plug 130b may travel/slide approximately 15.0 mm to approximately 20.0 mm between the first and second O-rings 119a, 119b. In various embodiments, the distance between the first and second O-rings 119a, 119b and/or the distance which the plug 130b travels/slides therebetween may be varied and/or adjusted based on the dimensions of a patient's heart, e.g., as determined by pre-operation measurements. In addition, to promote smooth movement (e.g., sliding and/or rotation) of the plug 130b, in various embodiments, the segment 117a of the middle portion 117 may be substantially straight.

In various embodiments, a medical device 100 of the present disclosure may have a sufficient length to extend from a tissue wall of the right ventricle (e.g., the septal apex) of a patient into the right atrium of the patient (e.g., the SVC/RA juncture). For example, in one embodiment, a medical device 100 of the present disclosure may have a total length ($L_1$) of approximately 65.0 mm, wherein a length ($L_2$) of the substantially rigid, non-slotted and non-heat set proximal portion 116 is approximately 10.0 mm, a length ($L_3$) of the slotted and heat-set middle portion 117 is approximately 50.0 mm, and a length ($L_4$) of the substantially rigid, non-slotted and non-heat set distal portion 118 is approximately 5.0 mm.

Referring to FIGS. 2A-2B, in one embodiment, a plug of the present disclosure may include a collapsed (e.g., constrained, delivery, etc.) configuration 130a (FIG. 2A) for insertion into and delivery through a delivery catheter 340 (FIG. 4), and an expanded (e.g., non-constrained, deployed, etc.) configuration 130b (FIG. 2B). In both the collapsed and expanded configurations, the plug 130a, 130b may include a central spine 136 defining a lumen 137 extending through a center of the plug. The lumen 137 may include an inner diameter ($d_2$) configured to slidably receive the outer diameter ($d_1$) of the tether 110, e.g., along the segment 117a of the middle portion 117 between the first and second O-rings 119a, 119b. Although the lumen 137 of the plug and the outer diameter of the tether, including segment 117a of the middle portion 117 are depicted as substantially circular, in various embodiments the outer dimension (e.g., shape) of tether 110 and the corresponding lumen 137 of plug 130 may include a variety of non-circular or non-spherical designs (e.g., square, rectangular, triangular, oblong/oval, etc.) such that the plug may be slidably but not rotatably disposed along the middle segment 117a.

Referring to FIG. 2B, in the expanded configuration, the plug 130b may include a varying outer diameter (e.g., conical, tapered, etc.) proximal portion 132 and a constant outer diameter (e.g., straight, parallel, etc.) distal portion 134. In various embodiments, all or a portion of a length ($L_5$) of the distal portion 134 may provide a surface (e.g., "landing zone") against which one or more leaflets of a regurgitating valve (e.g., a tricuspid or mitral valve) may contact (e.g., coapt) when the ventricle (e.g., right or left ventricle) is in the systole phase of the cardiac cycle. In one embodiment, the plug 130b of FIG. 2B may have an overall length of approximately 25.0 mm and a maximum width of approximately 10.0-15.0 mm. In various additional embodiments, a diameter and/or length of the distal portion 134 of the plug 130b may be adjusted (e.g., increased or decreased) based on the size, shape and/or severity of the regurgitating tricuspid valve. For example, the size, shape and/or severity of a regurgitating valve may, e.g., the effective regurgitant orifice area (EROA), may be determined via an echocardiogram prior to implanting a medical device 100 of the present disclosure. In addition, or alternatively, a dimension (e.g., size, shape, width, etc.) of the proximal portion 132 of the plug 130b may be adjusted to maximize an ability of the plug 130b to slide proximally and distally along the segment 117a of the middle portion 117 of the tether 110 during the diastole and systole phases of the cardiac cycle.

Referring to FIG. 3A, in one embodiment a plug of the present disclosure may be formed from a suitable shape memory tube 230 (e.g., nitinol), in which a first (e.g., distal) portion 236 of the tube 230 forms the central spine 136 (FIGS. 2A-2B), and a second (e.g., proximal) portion 238 of the tube 230 forms a framework which bends and/or folds back over the first portion 236. For example, referring to FIG. 3B, four evenly spaced cuts or slits (not shown) may be formed along a length of the second portion 238 to provide four separate/distinct and evenly spaced strips extending from the first portion 236. The four separate/distinct strips may then be distally bent and/or folded back to provide a framework extending over/along the first portion 236. Each of the separate/distinct strips which forms the framework may include a strut (e.g., body) 238a extending over/along a length of the first portion 236, and a tine 238b extending inward from an end of each strut 238a toward a distal end of the first portion 236. In various embodiments, a first section of each strut 238a may extend over/along the first portion 236 at an angle (e.g., to form the varying outer diameter proximal portion 132), and a second section of each strut 238a may extend over/along and parallel to the first portion 236 (e.g., to form the constant outer diameter distal portion 134).

Referring to FIG. 3C, in one embodiment, an impermeable cover or membrane 239 (e.g., ePTFE, polyurethane, or other polymer) may then be disposed or otherwise applied (e.g., coated, glued, shrink-wrapped, vacuum sealed, sewed, tied, extruded, e-spun, etc.) around an entire outer surface of the framework, and the tines 238b may then be attached (e.g., glued, adhered, bonded, welded, tacked, etc.) to the distal end of the first section 236 (e.g., the central spine 136) to form a plug configured to move between a collapsed and expanded configuration (as discussed above).

Although the plugs depicted in FIGS. 2B and 3C are formed from a framework comprising four struts 238a which are symmetrically spaced along/over the first portion 236 of the tube 230, in various embodiments the number, spacing, shape, thickness and/or curvature of the struts 238a may be varied based on the EROA of the regurgitating valve(s).

Referring to FIG. 4, in one embodiment, a system 300 of the present disclosure may include a medical device 100 (as discussed above) slidably disposed within a lumen 342 of a delivery catheter 340. The delivery catheter 340 may include a length sufficient to extend through the vasculature system of a patient to position the steerable distal end of the delivery catheter 340 at the proper location and orientation within the right ventricle of the patient (FIGS. 5A-5C). The tether 110 may be disposed within the lumen 342 of the delivery catheter 340 with the plug 130a maintained in the collapsed configuration between the first and second O-rings 119a, 119b. The retention members of the anchor 120 may extend distally beyond the distal end 114 of the tether 110 in a constrained (e.g., delivery) configuration 122a. In various embodiments, the anchor 120 may be disposed with an enlarged distal portion 346 of the delivery catheter 340. A push rod 344 may be disposed within the lumen 342 of the delivery catheter 340 proximal to (e.g., abutting) the proximal end 112 of the tether 110. In various embodiments, a user may from a proximal end (not shown) distally advance the push rod 344 to deploy the tether 110 (as discussed below) from within the lumen 342 of the delivery catheter 340. In various additional embodiments, a distal end of the push rod 344 may include receiving element (not shown) configured to reversibly receive a corresponding engagement member 113 (FIG. 1) on the proximal end of the tether 110. The reversible engagement between the receiving element and the engagement member 113 may allow the tether 110 to be held/maintained in firm/tight contact with the push rod 344 inside the delivery catheter to ensure that the tether is properly positioned (e.g., centered) across the tricuspid valve prior to and during delivery.

Referring to FIGS. 5A-5C, in use and by way of example, a system 300 of the present disclosure, including medical device 100 loaded therein, may be introduced into the vasculature of a patient (e.g., via the femoral vein) and the delivery catheter 340 advanced through the inferior vena cava 24 and into the heart 10 through the right atrium 12, across the tricuspid valve 16 and into the right ventricle 14. Referring to FIG. 5A, the delivery catheter 340 may then be advanced into the right ventricle and the steerable distal portion of the delivery catheter manipulated as necessary to place the distal end of the delivery catheter 340 in perpendicular contact with (e.g., normal to) a tissue wall (e.g., endocardial wall) of the right ventricle 14. For example, the distal end of the delivery catheter 340 may be placed in perpendicular contact with the septal apex of the right ventricle.

Referring to FIG. 5B, while maintaining direct contact with the tissue wall of the right ventricle 14, the push rod 344 may be distally advanced to move the retention members of the anchor 120 beyond the distal end of the delivery catheter 340, thereby placing a surface of the anchor 120 in contact with an inner wall of the right ventricle and advancing/penetrating each of the retention members 122b into the tissue wall of the right ventricle 14. As the full length of each retention member 122b moves beyond the distal end of the delivery catheter 340, each retention member 122b may sequentially move from a partially to fully unconstrained configuration to form hooks which embed within the tissue wall of the right ventricle without penetrating through (e.g., puncturing) the tissue wall.

Referring to FIG. 5C, while (optionally) maintaining the push rod 344 in firm contact with the proximal end 112 of the tether 110, the delivery catheter 340 may be proximally retracted into the right atrium 12 over/along the tether 110 to deploy the medical device 100 between the right atrium 12 and right ventricle 14 across the tricuspid valve 16. The delivery catheter 340 and push rod 344 may then be retracted through the vasculature and removed from the patient. In one embodiment, with the retention members of the anchor 120 embedded within the tissue wall of the right ventricle 14 in the unconstrained configuration 122b, the rigid distal portion 118 may maintain perpendicular contact between the anchor 120 and the tissue wall (e.g., apex of the septal wall) of the right ventricle 14. The slotted and heat-set middle portion 117 may move to one or more pre-determined heat-set angles (as discussed above), e.g., to provide 1) the proper angle of the middle portion 117 with the septal wall, 2) centering of the middle portion 117 across the tricuspid valve 16 and 3) the proper angle of the proximal portion 116 with in the SVC/RA juncture. The first and second O-rings 119a, 119b may be disposed on opposite sides of the tricuspid valve (e.g., the first O-ring 119a disposed in the right atrium 12, and the second O-ring 119b disposed within the right ventricle 14) such that the plug 130b in the second configuration is slidably disposed along the segment 117a of the middle portion 117.

Figure 6A:
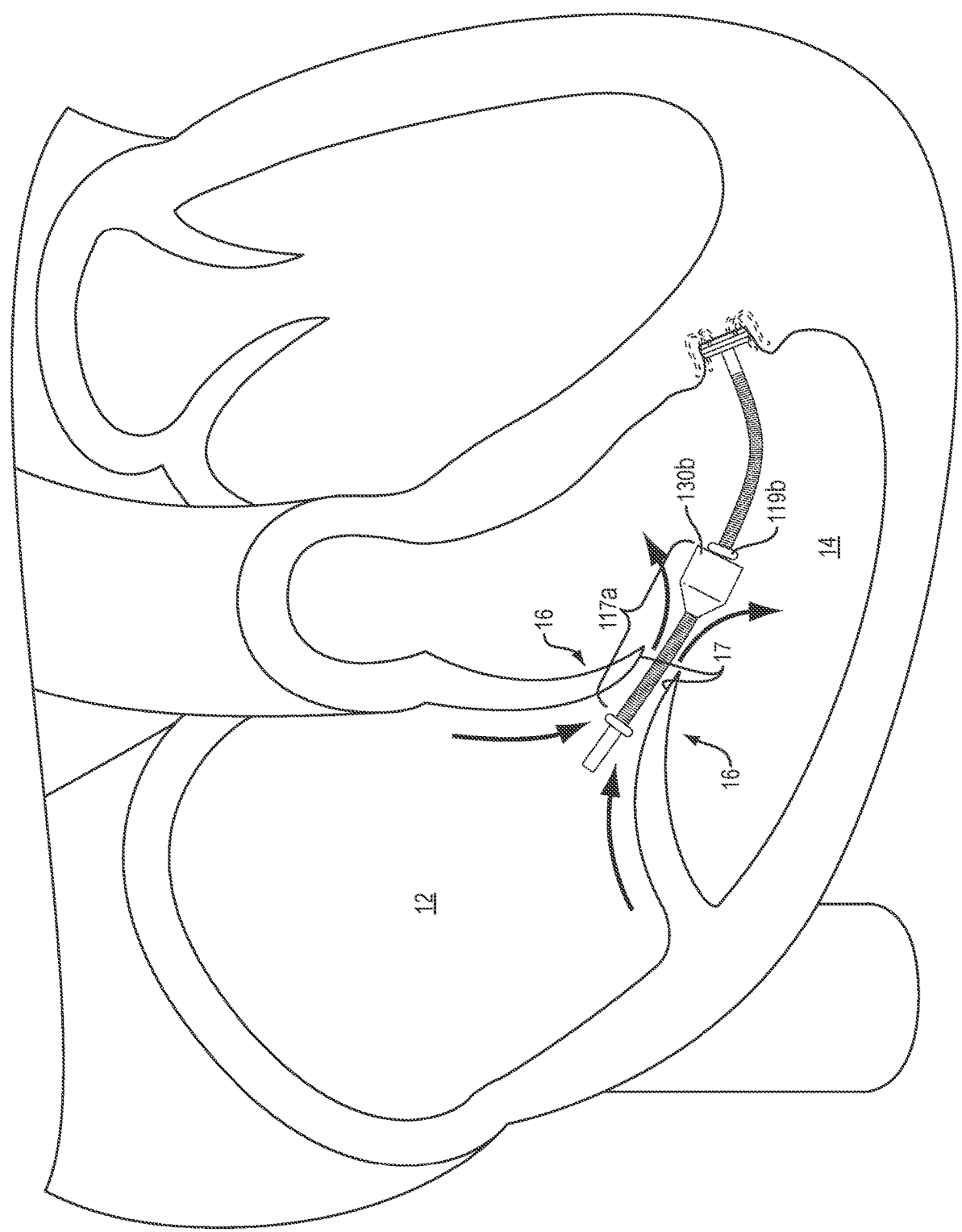
FIGS. 6A-6B provide schematic illustrations of a deployed medical device in use within the heart of a patient, according to one embodiment of the present disclosure.

Referring to FIG. 6A, in one embodiment, in the diastole phase of the cardiac cycle, the muscles of the right ventricle 14 relax and the leaflets 17 of the regurgitating tricuspid valve 16 open to draw/receive blood from the right atrium 12. The flow of blood through the regurgitating tricuspid valve 16 may force the plug 130b to slide distally along the segment 117a of the middle portion 117 to place a distal end of the plug 130b in contact with the second O-ring 119b. When disposed against the second O-ring 119b, no portion of the plug 130b is in contact with any of the leaflets 17 of the tricuspid valve 16, thereby allowing blood to freely flow into and fill the right ventricle 14.

Figure 6B:
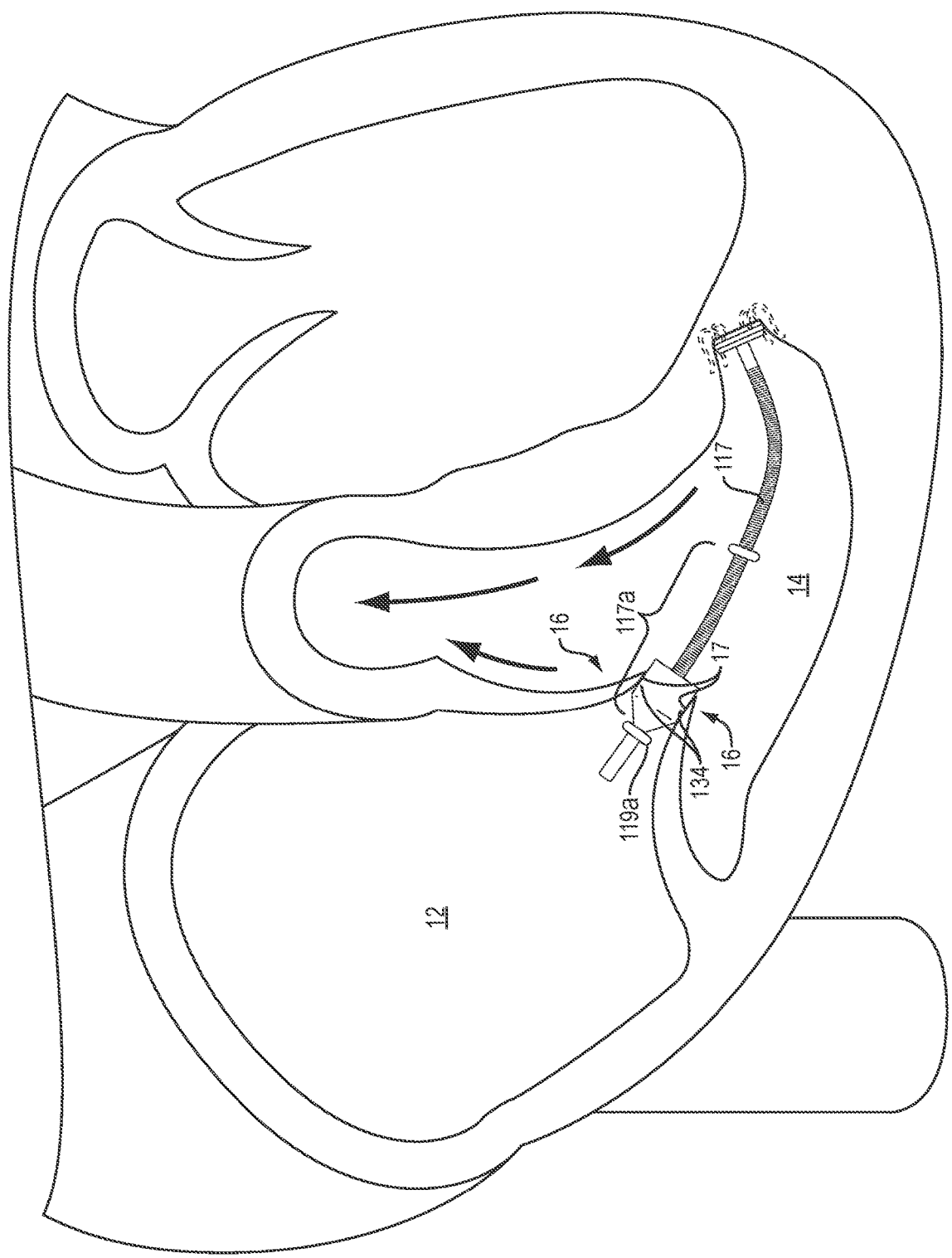

Referring to FIG. 6B, in one embodiment, in the systole phase of the cardiac cycle, the muscles of the right ventricle 14 contract and the leaflets 17 of the regurgitating tricuspid valve 16 close to pump blood from the right ventricle 14 into the pulmonary artery. The flow of blood from the right ventricle 14 into the pulmonary artery may force the plug 130b to slide proximally along the segment 117a of the middle portion 117 to place a proximal end of the plug 130b contact with the first O-ring 119a. A location/position of the first O-ring 119a along the middle portion 117 may be configured to position the plug 130b across the regurgitating tricuspid valve 16 such that the leaflets 17 of the regurgitating tricuspid valve 16 contact (e.g., coapt) an outer surface of the plug 130b along (all or a portion of) the constant outer diameter distal portion 134. The sealing contact between the leaflets 17 and the outer surface of the distal portion 134 of the plug 130b may effectively plug (e.g., close/seal) the regurgitant area to reduce or prevent the flow of blood back into (e.g., regurgitation) the right atrium 12 as the right ventricle 14 contracts.

In various embodiments, the plug 130b may slide distally and proximally along the proximal segment of the middle portion 117 during the repetitive diastole and systole phases of the normal cardiac cycle (e.g. pumping of the heart) to eliminate or significantly reduce regurgitation of blood across the tricuspid valve into the right atrium.

In various embodiments, all of a portion of exposed surfaces of the medical device 100, including the inner (e.g., spine) and outer surfaces (e.g., cover 294) of the plug 130a, 130b, may be coated or impregnated with one or more anti-thrombogenic agents to minimize the likelihood of thrombus formation between the plug 130b and tether 110. In addition, or alternatively, the tether 110 (including segment 117a) and the inner surface of the central spine 136 may be coated with or otherwise comprise a low friction material (e.g., Teflon™) to reduce drag/friction therebetween. In various other embodiments, the anchor 120 and/or retention members 122 may be coated or impregnated with one or more anti-inflammatory agents to reduce tissue irritating and/or scarring of the cardiac wall.

In various embodiments, a location/position of the first and second O-rings 119a, 119b along the middle portion 117, as well as the distance between the first and second O-rings 119a, 119b may be altered/optimized based, for example, on the individual flow characteristic of a patient's heart, the size/age of the patient and/or the patient's health. In addition, the segment 117a along which the plug 130b may proximally and distally slide is not necessarily defined by O-rings but may be defined by a variety of structural elements (e.g., limiting or stopping elements) and/or configurations, including, by way of non-limiting example, clip-on elements, increased diameter portions of the tether, flanges or tabs formed within or permanently attached to the tether, etc. In various embodiments, the first and/or second O-rings 119a, 119b may be formed from or otherwise include a metallic or radiopaque material to allow visualization of the medical device and/or plug 130b within the patient, e.g., during the procedure to place the medical device 100 within the patient, and to monitor the medical device 100 post-implantation.

In various other embodiments, a medical device 100 of the present disclosure may be removed or replaced, e.g., if the EROA of the regurgitating valve increases or decreases, or the patient ages and requires a longer tether. In addition, the plug 130b may be replaced (e.g., by removing the first O-ring 119a) without replacing the remainder of the medical device 100, e.g., if the plug 130b indicates signs of deterioration and/or if a plug 130b with different dimensions (e.g., larger or smaller) is required.

Although the delivery steps outlined in FIGS. 5A-5C, and the function of the medical device 100 outlined in FIGS. 6A-6B, depict the deployment and use of the medical device within the right atrium and right ventricle to treat a regurgitating tricuspid valve, the present disclosure is in no way limited to this chamber of the heart, but may also be used within the left atrium and left ventricle treat a regurgitating mitral valve.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A medical device, comprising:
    an elongate tether comprising a flexible middle portion and substantially rigid proximal and distal portions;
    an anchor disposed along a distal end of the tether and configured to engage a tissue wall of a right ventricle of a patient; and
    a plug slidably disposed along a proximal segment of the flexible middle portion.

2. The medical device of claim 1, wherein the flexible middle portion is slotted.

3. The medical device of claim 1, wherein the substantially rigid proximal and distal portions are not slotted.

4. The medical device of claim 1, wherein the flexible middle portion of the elongate tether is heat-set.

5. The medical device of claim 1, wherein the elongate tether includes a sufficient length to extend from the tissue wall of the right ventricle into the right atrium.

6. The medical device of claim 1, wherein the tether is configured to substantially center the proximal segment of the flexible middle portion across the tricuspid valve of a patient.

7. The medical device of claim 5, wherein the plug is configured to slide distally along the proximal segment of the middle portion when the right ventricle is in the diastole phase of the cardiac cycle, and the plug is configured to slide proximally along the proximal segment of the middle portion when the right ventricle is in the systole phase of the cardiac cycle.

8. The medical device of claim 1, wherein the proximal segment of the flexible middle portion is defined by first and second O-rings.

9. The medical device of claim 1, wherein the plug, when in a deployed configuration, includes a varying outer diameter proximal portion and a constant outer diameter distal portion.

10. The medical device of claim 1, wherein one or more leaflets of the tricuspid valve contact an outer surface of the plug when the right-ventricle is in the systole phase of the cardiac cycle.

11. The medical device of claim 1, wherein the plug does not contact any portion of the tricuspid valve when the right ventricle is in the diastole phase of the cardiac cycle.

12. The medical device of claim 1, wherein the anchor includes one or more retention members configured to move from a first configuration to a second configuration.

13. The medical device of claim 12, wherein the one or more retention members extend beyond the distal end of the tether in the first configuration, and at least a portion of the one or more retentions members extends over a segment of the rigid distal portion in the second configuration.

14. A plug, comprising:
a central spine defining a lumen therethrough configured to slidably receive a tether;
a framework extending over the central spine; and
an impermeable cover disposed around the framework;
wherein the plug is configured to move from a first configuration to a second configuration; and
wherein the framework, when in the second configuration, includes a varying outer diameter proximal portion and a constant outer diameter distal portion.

15. The plug of claim 14, wherein framework comprises:
at least one strut extending over the central spine; and
a tine extending inward from a distal end of each of the at least one struts;
wherein a distal end of each tine is configured to be attached to the central spine.

16. The plug of claim 15, wherein:
the central spine and framework are formed from a shape memory tube; and
wherein the at least one strut and the tine are formed as a plurality of cuts formed within in a first portion of the tube and folded back over a second portion of the tube.

17. The plug of claim 14, wherein the constant outer diameter distal portion of the plug, when in the second configuration, is configured to contact one or more leaflets of the tricuspid valve when in the systole phase of the cardiac cycle.

18. The plug of claim 14, wherein the plug is configured, when in the first configuration, to be slidably received within a lumen of a steerable delivery catheter.

19. A system, comprising:
a medical device slidably disposed within a lumen of a steerable delivery catheter, the medical device comprising:
an elongate tether comprising a flexible middle portion and substantially rigid proximal and distal portions;
an anchor disposed in a first configuration along a distal end of the tether; and
a plug disposed in a first configuration along a proximal segment of the flexible middle portion and slidable along the elongate tether; and
a push rod slidably disposed within the lumen of the steerable delivery catheter and proximal to the medical device.

20. The system of claim 19, wherein the anchor and the plug are configured to move from the first configuration to a second configuration when removed from constraint within the lumen of the steerable delivery catheter.

* * * * *